United States Patent
Ofosu-Asante et al.

(10) Patent No.: US 6,387,856 B1
(45) Date of Patent: May 14, 2002

(54) ANTIMICROBIAL DETERGENT COMPOSITIONS CONTAINING IODINE IONS

(75) Inventors: Kofi Ofosu-Asante, Cincinnati, OH (US); Jeffrey Edward Boucher, Beijing (CN); Marcus Wayne Evans, Hamilton, OH (US); David Robert Zint, Fort Thomas, KY (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/787,449

(22) PCT Filed: Sep. 16, 1999

(86) PCT No.: PCT/US99/21572

§ 371 Date: Mar. 19, 2001

§ 102(e) Date: Mar. 19, 2001

(87) PCT Pub. No.: WO00/18867

PCT Pub. Date: Apr. 6, 2000

Related U.S. Application Data

(60) Provisional application No. 60/101,791, filed on Sep. 25, 1998.

(51) Int. Cl.$^7$ .............................. C11D 3/24; C11D 1/75
(52) U.S. Cl. ................. 510/131; 510/132; 510/161; 510/238; 510/235; 510/385; 510/503
(58) Field of Search ................... 510/131, 132, 510/161, 238, 235, 385, 503

(56) References Cited

U.S. PATENT DOCUMENTS

| | | | | |
|---|---|---|---|---|
| 3,534,102 A | * | 10/1970 | Waldstein | 260/584 |
| 3,950,261 A | * | 4/1976 | Landi et al. | 252/106 |
| 4,045,364 A | * | 8/1977 | Richter | 252/106 |
| 4,206,204 A | * | 6/1980 | Langford | 424/150 |
| 4,207,310 A | | 6/1980 | Langford | |
| 4,355,021 A | | 10/1982 | Mahl et al. | |
| 4,597,975 A | * | 7/1986 | Woodward et al. | 424/150 |
| 5,707,955 A | * | 1/1998 | Gomes et al. | 510/421 |

* cited by examiner

Primary Examiner—Charles Boyer
(74) Attorney, Agent, or Firm—C. Bryant Cook; Kim W. Zerby; Steve W. Miller

(57) ABSTRACT

Antimicrobial detergent compositions especially suitable for manual diswashing comprise 0.001–2% iodine ions complexed with an amphoteric surfactant, 5–90% uncomplexed surfactant selected from the group consisting of anionic surfactants, nonionic surfactants, amphoteric surfactants and mixture thereof, and 5–50% water. The detergent compositions have pH of 7–10. Preferably at least a portion of the iodine ions are added as an iodine in the form of a compound selected from the group consisting of KI, NaI, KOI, NaOI and Ca(OI)2.

10 Claims, No Drawings

ANTIMICROBIAL DETERGENT COMPOSITIONS CONTAINING IODINE IONS

This application is a 371 of PCT US99/21572 filed Sep. 16, 1999 which claims benefit of provisional application No. 60/101,791 filed Sep. 25, 1998.

TECHNICAL FIELD

The present invention relates to liquid dishwashing detergent compositions containing surfactants and iodine disinfectant. More specifically, the invention relates to compositions and a method for removing soils and sanitizing (significantly reducing microorganism populations) plastics, dishware, countertops, fabric, wood surfaces, and other substrates by applying a light duty liquid detergent composition which preferably comprises a complex of a surfactant with iodine in the form of an iodophor.

BACKGROUND OF THE INVENTION

Light-duty liquid (LDL) or gel detergent compositions useful for manual dishwashing are well known in the art. Such products are generally formulated to provide a number of widely diverse performance and aesthetics properties and characteristics. First and foremost, liquid or gel dishwashing products must be formulated with types and amounts of surfactants and other cleaning adjuvants that will provide acceptable solubilization and removal of food soils, especially greasy soils, from dishware being cleaned with, or in aqueous solutions formed from, such products. Furthermore, any resultant liquid diswashing product must be stable and not subject to adverse heterogeneity.

In light of increasingly frequent and widespread incidents of contamination of meat and vegetable products, possible contamination of soiled hard surfaces like dishware by infectious microbes can present special problems during manual dishwashing. Articles such as plates, utensils, pots, pans, crockery and the like may be contaminated by virulent strains of microbes such as *Stahylococcus aureus, Escierichia coli*, and members of the Salmonella genus. In view of this possible contamination on dishware, light duty liquid dishwashing detergents with antimicrobial properties are currently much desired by consumers. When microbe-contaminated dishware is to be manually cleaned, very often highly concentrated, or high concentrations of, dishwashing detergent products are used. During such applications, the presence of an antimicrobal, disinfecting agent in the dishwashing detergent composition can have a significant effect on the composition's ability to disinfect and sanitize the dishware.

In addition to being useful for cleaning and sanitizing dishware, LDL compositions will also desirably possess other attributes that enhance the aesthetics or consumer perception of the effectiveness of the manual dishwashing operation. Thus, useful hand dishwashing liquids should also employ materials that combine to form a clear and odorless detergent liquid. This allows greater control over the detergent's final aesthetic qualities through the use of perfumes and colorants. In addition, detergent products should not leave a stain or any other unattractive artifact on dishware which might compromise the overall consumer perception of the detergents' aesthetic qualities.

Given the foregoing, there is a continuing need to formulate manual dishwashing liquids and gels that provide an acceptable and desirable balance between cleaning and sanitization performance, in both concentrated direct application and aqueous washing solution contexts, and product aesthetics. Accordingly, it is an object of the present invention to provide light-duty liquid dishwashing compositions which are especially effective at sanitizing microbe-containing dishware when such compositions are used in the context of a manual dishwashing operation.

Iodine is a well known disinfectant which has previously been added to liquid dishwashing compositions to provide antimicrobial protection. By adding an antimicrobial agent, such compositions can provide disinfecting properties against a broad variety of microorganisms. However, the addition of such antimicrobial agents may undermine certain critical properties of a dishwashing detergent composition. In particular, the addition of iodine to a LDL has been shown to undermine the product's stability. Iodine itself is unstable in compositions having a pH greater than about 7 and above. Furthermore, dishwashing compositions made with iodine take on an unattractive color and odor which make them aesthetically unacceptable. Such unacceptable colors and odors cannot be changed to the desirable LDL color and scent with perfumes and colorants. Finally, iodine may cause the staining of dishware treated with iodine-containing detergent compositions.

It is thus a further object of the present invention to provide stable, light-duty liquid dishwashing compositions containing iodine which are especially effective at sanitizing microbe-containing dishware, are clear and odorless before the addition of perfume and colorants and do not leave iodine stains on treated dishware. Under the present invention, iodine is stable even in compositions with a pH of in excess of 7.

Iodine may be complexed with surfactants to form a complex molecule known as an "iodophor." While not intending to be limited by theory, there are two different mechanisms which have been explained this complexation. In the first mechanism, the iodine-surfactant complex is formed by weak interaction between the free electrons on iodine or electrostatic interaction between triiodide, generated via a reaction of iodide and iodine, and the overall net positive charge on the amphoteric surfactant. In the second mechanism the resulting complex is formed because iodine molecules may be trapped inside micelles formed from the surfactant.

It has been found in the present invention that when amphoteric surfactants, such as amine oxide, are complexed with iodine to form an iodophor complex, then the deleterious consequences of the addition of iodine are ameliorated. While maintaining its antimicrobial properties, the detergent composition suffers no loss in cleaning efficacy or stability and is in the form of a clear liquid with no unpleasant odor.

Iodophors provide these benefits on the account of the fact that when iodine is complexed with another molecule to form an iodophor, it loses its separate chemical identity and most of its elemental properties. Thus, while the iodophor maintains the same disinfection and sanitization benefits of free iodine, it does not have any of the latter's tendency to cause discoloration, malodors or dishware staining. Additionally, while iodine is very volatile, iodophors are not, thus greatly improving stability of iodophor containing LDL compositions.

The benefits of this invention can be provided for and included in a broader range of products than just LDLs. Such products include may liquid hand soap and moist paper or fabric wipes where a formulation according to the present invention is contained in the wipe as a germicide.

SUMMARY OF THE INVENTION

The present invention relates to a light-duty liquid dishwashing detergent compositions having especially desirable antimicrobial and sanitization performance. Such compositions comprise, by weight: (a) from about 0.001% to about 2.0% of an iodine powder, wherein at least a portion of the iodine powder is complexed iodine that is complexed with a complexing amphoteric surfactant, (b) from about 5% to about 90% of additional, uncomplexed surfactants which may include anionic surfactants, nonionic surfactants, amphoteric surfactants and mixtures thereof; and (c) from about 5% to about 50% water. This light duty liquid detergent composition has a pH of between about 7 and about 10.

The complexing amphoteric surfactant essentially comprises semi-polar amine oxide surfactants.

The uncomplexed anionic surfactant essentially comprises alkyl ether sulfates containing from about 8 to 18 carbon atoms in the alkyl group. These alkyl ether sulfates also contain from about 1 to 6 moles of ethylene oxide per molecule.

The uncomplexed nonionic surfactant essentially comprises $C_{8-18}$ polyhydroxy fatty acids amides. In the nonionic surfactant components such as polyhydroxy fatty acids amides may also be combined with from about 0.2% to 2% of the composition of a nonionic co-surfactant. This nonionic co-surfactant is selected from $C_{8-18}$ alcohol ethoxylates having from about 1 to 15 moles of ethylene oxide, ethylene oxide-propylene oxide block co-polymer surfactants and combinations of these nonionic co-surfactants.

The foregoing essential components, as well as a number of additional optional ingredients, can be combined in any conventional manner to form the light-duty liquid or gel dishwashing detergent products of this invention.

The present invention, when used according to the method described and claimed herein, provides a liquid dish detergent that has not only excellent cleaning performance but also exceptional antimicrobial protection against a broad array of microorganisms.

Yet another advantage of this invention is that the composition, before the addition of perfumes and colorants, is clear and odorless as well as having good long-term compositional stability and homogeneity and causing no appreciable dish-staining.

DETAILED DESCRIPTION OF THE INVENTION

Definitions—As used herein the terms "disinfection", "sanitization" and "antimicrobial protection" are intended to mean killing microbes commonly found in household kitchens and houses. Examples of various microbes include: germs, bacteria, viruses, parasites, and fungi/spores. Preferably the detergent compositions used herein contact the substrate for a sufficient time to significantly reduce the amount of microbes on the substrate. By "significant reduction" it is meant that at least about 50% of the microbes on the substrate are killed or otherwise rendered inactive, preferably the amount of microbes on the substrate is reduced by at least about 90%, and most preferably the amount of microbes on the substrate is reduced by at least about 99.9%. A "disinfectant" or "disinfecting agent" is intended to refer to a substance which provides such "disinfection", "sanitization" and "antimicrobial protection".

As used herein the term "light duty liquid detergent composition" refers to those compositions which are employed in manual (i.e. hand) dishwashing.

Uncomplexed Detersive Surfactants

The compositions of this invention comprise from about 5% to about 90%, more preferably from about 25% to about 70% by weight surfactant.

These surfactants contribute foaming, detergency, and/or mildness to the composition. Included in this category are several anionic surfactants commonly used in liquid or gel dishwashing detergents. The cations associated with these anionic surfactants can be alkali metal, diamines, mono-, di-, and tri-ethanoldiamines, preferably sodium, potassium, diamines and mixtures thereof. Examples of anionic surfactants that are useful in the present invention are the following classes:

(1) Alkyl benzene sulfonates in which the alkyl group contains from 9 to 15 carbon atoms, preferably 11 to 14 carbon atoms in straight chain or branched chain configuration. An especially preferred linear alkyl benzene sulfonate contains about 12 carbon atoms. U.S. Pat. Nos. 2,220,099 and 2,477,383 describe these surfactants in detail.

(2) Alkyl sulfates obtained by sulfating an alcohol having 8 to 22 carbon atoms, preferably 12 to 16 carbon atoms. The alkyl sulfates have the formula $ROSO_3^-M^+$ where R is the $C_{8-22}$ alkyl group and M is a mono- and/or divalant cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. U.S. Pat. No. 3,332,880 contains a description of suitable olefin sulfonates.

(5) Alkyl ether sulfates derived from ethoxylating an alcohol having 8 to 22 carbon atoms, preferably 12 to 16 carbon atoms, less than 30, preferably less than 12, moles of ethylene oxide. The alkyl ether sulfates having the formula:

$$RO(C_2H_2O)_xSO_3^-M^{n-}$$

where R is a $C_{8-22}$ alkyl group, x is 1–30, n is 1 or 2 and M is a mono- or divalent cation.

(6) Alkyl glyceryl ether sulfonates having 8 to 22 carbon atoms, preferably 12 to 16 carbon atoms, in the alkyl moiety.

(7) Fatty acid ester sulfonates of the formula:

$$R^1—CH(SO_3^-M^{n+})CO_2R^2$$

wherein $R^1$ is straight or branched alkyl from about $C_8$ to $C_{18}$, preferably $C_{12}$ to $C_{16}$, and $R^2$ is straight or branched alkyl from about $C_1$ to $C_6$, preferably primarily $C_1$, and n is 1 or 2.

(8) Secondary alcohol sulfates having 6 to 18, preferably 8 to 16 carbon atoms.

(9) Alkyl ethoxy carboxylates of the present invention are of the generic formula $$RO(CH_2CH_2O)_xCH_2COO^-M^{n+}$$

wherein R is a $C_{1-6}$ alkyl group, x ranges from 0 to about 10, n is 1 or 2 and the ethoxylate distribution is such that, on a weight basis, the amount of material where x is 0 is less than about 20%, preferably less than about 15%, most preferably less than about 10%, and the amount of material where x is greater than 7 is less than about 25%, preferably less than about 15%, most preferably less than about 10%, the average x is from about 2 to 4 when the average R is $C_{13}$ or less, and the average x is from about 3 to 6 when the average R is greater than $C_{13}$, and M is a cation, preferably chosen from alkali metal, diamines, mono-, di-, and tri-ethanoldiamines, most preferably from sodium, potassium, diamines, and mixtures thereof with magnesium ions. The preferred alkyl ethoxy carboxylates are those where R is a $C_{12}$ to $C_{14}$ alkyl group. Suitable processes for preparing the alkyl ethoxy carboxylates are disclosed in U.S. Pat. No. 5,233,087, incorporated herein by reference.

(10) The following general structures illustrate some of the special soaps (or their precursor acids) employed in this invention.

A. A highly preferred class of soaps used herein comprises the $C_{10}$–$C_{16}$ secondary carboxyl materials of the formula $R^3$ CH($R^4$)COOM, wherein $R^3$ is $CH_3$ $(CH_2)_x$ and $R^4$ is $CH_3$ $(CH_2)_y$, wherein y can be 0 or an integer from 1 to 6, x is an integer from 6 to 12 and the sum of (x+y) is 6–12, preferably 7–11, most preferably 8–9.

B. Another class of special soaps useful herein comprises those carboxyl compounds wherein the carboxyl substituent is on a ring hydrocarbyl unit, i.e., secondary soaps of the formula

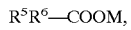

wherein $R^5$ is $C_7$–$C_{10}$, preferably $C_8$–$C_9$, alkyl or alkenyl and $R^6$ is a ring structure, such as benzene, cyclopentane, cyclohexane, and the like. (Note: $R^5$ can be in the ortho, meta or para position relative to the carboxyl on the ring.)

C. Still another class of soaps includes the $C_{10}$–$C_{18}$ primary and secondary carboxyl compounds of the formula $R^7$CH($R^8$)COOM, wherein the sum of the carbons in $R^7$ and $R^8$ is 8–16, $R^7$ is of the form $CH_3$—$(CHR^9)_x$ and $R^8$ is of the form H—$(CHR^9)_y$, where x and y are integers in the range 0–15 and $R^9$ is H or a $C_{1-4}$ linear or branched alkyl group. $R^9$ can be any combination of H and $C_{1-4}$ linear or branched alkyl group members within a single —$(CHR^9)_{x,y}$ group; however, each molecule in this class must contain at least one $R^9$ that is not H. These types of molecules can be made by numerous methods, e.g. by hydroformylation and oxidation of branched olefins, hydroxycarboxylation of branched olefins, oxidation of the products of Guerbet reaction involving branched oxoalcohols. The branched olefins can be derived by igomerization of shorter olefins, e.g. butene, isobutylene, branched hexene, propylene and pentene.

D. Yet another class of soaps includes the $C_{10}$–$C_{18}$ tertiary carboxyl compounds, e.g., neo-acids, of the formula $R^{10}CR^{11}$ ($R^{12}$)COOM, wherein the sum of the carbons in $R^{10}$, $R^{11}$ and $R^{12}$ is 8–16. $R^{10}$, $R^{11}$ and $R^{12}$ are of the form $CH_3$—$(CHR^{13})_x$, where x is an integer in the range 0–13, and $R^{13}$ is H or a $C_{1-4}$ linear or branched alkyl group. Note that $R^{13}$ can be any combination of H and $C_{1-4}$ linear or branched alkyl group members within a single —$(CHR^{13})_x$ group. These types of molecules result from addition of a carboxyl group to a branched olefin, e.g., by the Koch reaction. Commercial examples include the neodecanoic acid manufactured by Exxon, and the Versatic.™. acids manufactured by Shell.

In each of the above formulas A, B, C and D, the species M can be any suitable, especially water-solubilizing, counterion, e.g., H, alkali metal, alkaline earth metal, diamines, alkanoldiamines, di- and tri-alkanoldiamines, $C_1$–$C_5$ alkyl substituted diamines and the like. Sodium is convenient, as is diethanoldiamines.

Preferred secondary soaps for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid; 2-pentyl-1-heptanoic acid; 2-methyl-1-dodecanoic acid; 2-ethyl-1-undecanoic acid; 2-propyl-1-decanoic acid; 2-butyl-1-nonanoic acid; 2-pentyl-1-octanoic acid and mixtures thereof.

(11) Mixtures thereof.

The above described anionic surfactants are all available commercially. It should be noted that although both dialkyl sulfosuccinates and fatty acid ester sulfonates will function well at neutral to slightly alkaline pH, they will not be chemically stable in a composition with pH much greater than about 8.5. It should also be noted that sulfate impurities may be present due to hydrolysis of alkyl sulfates, alkyl ether sulfates or reaction of trapped $SO_3^-$ from the sulfation or sulfonation process with water. The sulfate contaminant may be detrimental with respect to stability of the product. It is therefore an important consideration that the anionic surfactant used in this embodiment contain very low levels (i.e. less than 1% preferably from 0 to about 0.6%, more preferably from 0 to about 0.3%), if any, sulfate ion impurity.

Examples of nonionic detergent surfactants that are useful in the present invention are generally disclosed in U.S. Pat. No. 3,929,678, Laughlin et al., issued Dec. 30, 1975, at column 13, line 14 through column 16, line 6, incorporated herein by reference. Exemplary, non-limiting classes of useful nonionic surfactants are listed below.

1. The polyethylene, polypropylene, and polybutylene oxide condensates of alkyl phenols. In general, the polyethylene oxide condensates are preferred. These compounds include the condensation products of alkyl phenols having an alkyl group containing from 6 to 12 carbon atoms in either a straight- or branched-chain configuration with the alkylene oxide. Commercially available nonionic surfactants of this type include Igepal.™. CO-630, marketed by the GAF Corporation; and Triton.™. X45, X-45, X-114, X-100, and X-102, all marketed by the Rohm & Haas Company.

2. Alcohol ethoxylates which are the condensation products of aliphatic alcohols with from about 1 to about 25 moles of ethylene oxide. They are represented by the general formula:

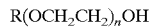

wherein R is a $C_{12-16}$ alkyl group and n ranges from 0 to about 10 and the average n is less than 6. Such materials have been commercially marketed under the tradenames Neodol 25-7 and Neodol 23-6.5 by Shell Chemical Company. Other useful Neodols include Neodol 1-5, ethoxylated fatty alcohol averaging 11 carbon atoms in its alkyl chain with about 5 moles of ethylene oxide; Neodol 23-9, an ethoxylated primary $C_{12}$–$C_{13}$ alcohol having about 9 moles of ethylene oxide and Neodol 91-10, an ethoxylated $C_9$–$C_{11}$ primary alcohol having about 10 moles of ethylene oxide. Alcohol ethoxylates of this type have also been marketed by Shell Chemical Company under the Dobanol tradename. Dobanol 91-5 is an ethoxylated $C_9$–$C_{11}$ fatty alcohol with an average of 5 moles ethylene oxide and Dobanol 25-7 is an ethoxylated $C_{12}$–$C_{15}$ fatty alcohol with an average of 7 moles of ethylene oxide per mole of fatty alcohol.

Other examples of suitable ethoxylated alcohol nonionic surfactants include Tergitol 15-S-7 and Tergitol 15-S-9, both of which are secondary alcohol ethoxylates that have been commercially marketed by Union Carbide Corporation. The former is a mixed ethoxylation product of $C_{11}$ to $C_{15}$ linear secondary alkanol with 7 moles of ethylene oxide and the latter is a similar product but with 9 moles of ethylene oxide being reacted.

Other types of alcohol ethoxylate nonionics useful in the present compositions are higher molecular weight nonionics, such as Neodol 45-11, which are similar ethylene oxide condensation products of higher fatty alcohols, with the higher fatty alcohol being of 14–15 carbon atoms and the number of ethylene oxide groups per mole being about 11. Such products have also been commercially marketed by Shell Chemical Company.

Ethoxylated alcohol nonionic co-surfactants will frequently comprise from about 0.2% to 2% of the compositions herein. More preferably, such ethoxylated alcohols will comprise from about 0.5% to 1.5% of the compositions.

3. Another type of nonionic co-surfactant suitable for use in combination with the polyhydroxy fatty acid amides in the nonionic surfactant component herein comprises the ethylene oxide-propylene oxide block co-polymers that function as polymeric surfactants. Such block co-polymers comprise one or more groups which are hydrophobic and which contain mostly ethylene oxide moieties and one or more hydrophobic groups which contain mostly propylene oxide moieties. Such groups are attached to the residue of a compound that contained one or more hydroxy groups or amine groups. Such polymeric surfactants have a molecular weight ranging from about 400 to 60,000.

Preferred ethylene oxide-propylene oxide polymeric surfactants are those in which propylene oxide is condensed with an amine, especially a diamine, to provide a base that is then condensed with ethylene oxide. Materials of this type are marketed under the tradename Tetronic®. Similar structures wherein the ethylene diamine is replaced with a polyol such as propylene glycol are marketed under the tradename "Pluronic®". Preferred ethylene oxide-propylene oxide (EO-PO) polymeric surfactants have an HLB which ranges from about 4 to 30, more preferably about 10 to 20.

The ethylene oxide-propylene oxide block co-polymers used herein are described in greater detail in Pancheri/Mao, U.S. Pat. No. 5,167,872; Issued Dec. 2, 1992. This patent is incorporated herein by reference.

Ethylene oxide-propylene oxide block co-polymers will frequently be present to the extent of from about 0.1% to 2% of the compositions herein. More preferably, these polymeric surfactant materials will comprise from about 0.2% to 0.8% of the compositions herein.

4. The condensation products of ethylene oxide with a hydrophobic base formed by the condensation of propylene oxide with propylene glycol. The hydrophobic portion of these compounds preferably has a molecular weight of from about 1500 to about 1800 and exhibits water insolubility.

5. Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. U.S. Pat. Nos. 4,373,203 and 4,732,704, incorporated herein by reference, also describe acceptable surfactants.

Examples of Zwitterionic detergent surfactants that are useful in the present invention include derivatives of aliphatic quaternary diamines, phosphonium, and sulphonium compounds in which the aliphatic moiety can be straight or branched chain and wherein one of the aliphatic substituents contains from about 8 to 24 carbon atoms and one contains an anionic water-solubilizing group. Particularly preferred zwitterionic materials are the ethoxylated diamines sulfonates and sulfates disclosed in U.S. Pat. No. 3,925,262, Laughlin et al, issued Dec. 9, 1975 and U.S. Pat. No. 3,929,262. Laughlin et al, issued Dec. 30, 1975, said patents being incorporated herein by reference.

Non-limiting examples of amphoteric detergent surfactants that are useful in the present invention include:

1. Amido propyl betaines.
2. Derivatives of aliphatic or heterocyclic secondary and ternary amines in which the aliphatic moiety can be straight chain or branched and wherein one of the aliphatic substituents contains from about 8 to about 24 carbon atoms and at least one aliphatic substituent contains an anionic water-solubilizing group.
3. Amine oxides, such as propyl amine oxides, represented by the formula:

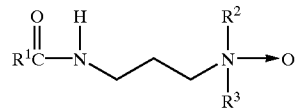

wherein $R_1$ is an alkyl, 2-hydroxyalkyl, 3-hydroxyalkyl, or 3-alkoxy-2-hydroxypropyl radical in which the alkyl and alkoxy, respectively, contain from about 8 to about 18 carbon atoms, $R_2$ and $R_3$ are each methyl, ethyl, propyl, isopropyl, 2-hydroxyethyl, 2-hydroxypropyl, or 3-hydroxypropyl and n is from 0 to about 10.

Preferred species of amphoteric surfactants include amine oxide semi-polar nonionic surface active agents comprising compounds and mixtures of compounds having the formula:

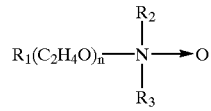

wherein $R_1$ is an alkyl, 2-hydroxyalkyl, 3-hydroxyalkyl, or 3-alkoxy-2-hydroxypropyl radical in which the alkyl and alkoxy, respectively, contain from about 8 to about 18 carbon atoms, $R_2$ and $R_3$ are each methyl, ethyl, propyl, isopropyl, 2-hydroxyethyl, 2-hydroxypropyl, or 3-hydroxypropyl and n is from 0 to about 10. Particularly preferred are amine oxides of the formula:

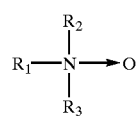

wherein $R_1$ is a $C_{10-14}$ alkyl and $R_2$ and $R_3$ are methyl or ethyl.

Disinfection Agent and Complexing Surfactants

The compositions of this invention comprise a disinfectant, iodine, in amounts of about 0.001% to about 2.0%, preferably from about 0.001% to 0.5% by weight of the composition. The iodine is preferably present in the form of iodine powder, but may also be added as an iodide in the form of compounds such as KI, NaI, KOI, NaOI, Ca(OI)$_2$. Thus the compositions of the instant invention may comprise iodide, iodine or mixtures thereof. At least a portion of the iodine or iodide powder is complexed with a complexing surfactant to form an iodophor.

The complexing surfactants that are useful in the present invention include any of the aforementioned amphoteric and nonionic surfactants. Amphoteric surfactants may be used as the sole complexing surfactant. In such a case, the iodine-surfactant complex is formed by weak interaction between the free electrons on iodine or electrostatic interaction between triiodide, generated via a reaction of iodide and iodine, and the overall net positive charge on the amphoteric surfactant. When nonionic surfactants are used as complexing surfactants they are used in combination with amphoteric surfactants; creating a mixture of complexing amphoteric and nonionic surfactants. When iodophor complexes are formed from nonionic surfactants the resulting complex is formed because iodine molecules may be trapped inside micelles formed from the surfactant. Preferred species of nonionic surfactants include the alcohol ethoxylates surfactants mentioned above Preferred species of amphoteric surfactants include the amine oxide semi-polar nonionic surfactants mentioned above.

Calcium or Magnesium Ions

The presence of calcium and/or magnesium (divalent) ions improves the cleaning of greasy soils for various compositions, i.e. compositions containing alkyl ethoxy carboxylates and/or polyhydroxy fatty acid amide. This is especially true when the compositions are used in softened water that contains few divalent ions. It is believed that calcium and/or magnesium ions increase the packing of the surfactants at the oil/water interface, thereby reducing interfacial tension and improving grease cleaning.

Compositions of the invention hereof containing magnesium and/or calcium ions exhibit good grease removal, manifest mildness to the skin, and provide good storage stability. The ions are present in the compositions hereof at an active level of from about 0.1% to 4%, preferably from about 0.3% to 3.5%, more preferably from about 0.5% to 1%, by weight.

Preferably, the magnesium or calcium ions are added as a hydroxide, chloride, acetate, formate, oxide or nitrate salt to the compositions of the present invention.

The amount of calcium or magnesium ions present in compositions of the invention will be dependent upon the amount of total surfactant present therein, including the amount of alkyl ethoxy carboxylates and polyhydroxy fatty acid amide. When calcium ions are present in the compositions of this invention, the molar ratio of calcium ions to total anionic surfactant is from about 0.25:1 to about 2:1 for compositions of the invention.

Formulating such divalent ion-containing compositions in alkaline pH matrices may be difficult due to the incompatibility of the divalent ions, particularly magnesium, with hydroxide ions. When both divalent ions and alkaline pH are combined with the surfactant mixture of this invention, grease cleaning is achieved that is superior to that obtained by either alkaline pH or divalent ions alone. Yet, during storage, the stability of these compositions becomes poor due to the formation of hydroxide precipitates. Therefore, chelating agents discussed herein below may also be necessary.

Solvents

The solvents that may be used in the present invention include water, lower molecular weight alcohols such as ethyl alcohol, isopropyl alcohol, etc. In liquid detergent compositions there will typically be from 0% to about 90%, preferably from about 20% to about 70%, most preferably from about 40% to about 60% of water, and from 0% to about 50%, most preferably from about 3% to about 10% of ingredients to promote solubility, including ethyl or isopropyl alcohol, conventional hydrotropes, etc.

Suds Booster

Another component which may be included in the composition of this invention is a suds stabilizing surfactant (suds booster) at a level of less than about 15%, preferably from about 0.5% to 12%, more preferably from about 1% to 10% by weight of the composition. Optional suds stabilizing surfactants operable in the instant' composition are: sultaines, complex betaines, betaines, ethylene oxide condensates, fatty acid amides, amine oxide semi-polar nonionics, and cationic surfactants. This invention includes within its scope high-foaming detergent composition embodiments.

The composition of this invention can contain betaine detergent surfactants having the general formula:

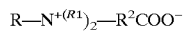

$$R-N^{+(R^1)}{}_2-R^2COO^-$$

wherein R is a hydrophobic group selected from the group consisting of alkyl groups containing from about 10 to about 22 carbon atoms, preferably from about 12 to about 18 carbon atoms, alkyl aryl and aryl alkyl groups containing a similar number of carbon atoms with a benzene ring being treated as equivalent to about 2 carbon atoms, and similar structures interrupted by amido or ether linkages; each $R^1$ is an alkyl group containing from 1 to about 3 carbon atoms; and $R^2$ is an alkylene group containing from 1 to about 6 carbon atoms.

Examples of preferred betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethyldiamines hexanoate. Other suitable suds boosters are disclosed in U.S. Pat. Nos. 3,950,417; 4,137,191; 4,375,421; 5,415,814 and British Patent GB No. 2,103,236, all of which are incorporated herein by reference.

It will be recognized that the alkyl (and acyl) groups for the above betaine surfactants can be derived from either natural or synthetic sources, e,g., they can be derived from naturally occurring fatty acids, olefins such as those prepared by Ziegler, or Oxo processes; or from olefins separated from petroleum either with or without "cracking".

The sultaines useful in the present invention are those compounds having the formula $(R(R^1)^2 N^{-R^2}SO_3^-$ wherein R is a $C_{6-18}$ hydrocarbyl group, preferably a $C_{10-16}$ alkyl group, more preferably a $C_{12-13}$ alkyl group, each $R^1$ is typically $C_{1-3}$ alkyl, preferably methyl, and $R^2$ is a $C_{1-6}$ hydrocarbyl group, preferably a $C_{1-3}$ alkylene or, preferably, hydroxyalkylene group. Examples of suitable sultaines include $C_{12-14}$ dimethylammonio-2-hydroxypropyl sulfonate, $C_{12-14}$ amido propyl ammonio-2-hydroxypropyl sultaine, $C_{12-14}$ dihydroxyethylammonio propane sulfonate, and $C_{16-18}$ dimethylammonio hexane sulfonate, with $C_{12-14}$ amido propyl ammonio-2-hydroxypropyl sultaine being preferred.

The ethylene oxide condensates are broadly defined as compounds produced by the condensation of ethylene oxide groups (hydrophilic in nature) with an organic hydrophobic compound, which can be aliphatic or alkyl aromatic in nature. The length of the hydrophilic or polyoxyalkylene radical which is condensed with any particular hydrophobic group can be readily adjusted to yield a water-soluble compound having the desired balance between hydrophilic and hydrophobic elements.

Examples of such ethylene oxide condensates suitable as suds stabilizers are the condensation products of aliphatic alcohols with ethylene oxide. The alkyl chain of the aliphatic alcohol can either be straight or branched and generally contains from about 8 to about 18, preferably from about 8 to about 14, carbon atoms for best performance as suds stabilizers. the ethylene oxide being present in amounts of from about 8 moles to about 30, preferably from about 8 to about 14 moles of ethylene oxide per mole of alcohol.

Examples of the amide surfactants useful herein include the ammonia, monoethanol, and diethanoi amides of fatty acids having an acyl moiety containing from about 8 to about 18 carbon atoms and represented by the general formula:

$$R^1—CO—N(H)_{m-1}(R^2OH)_{3-m}$$

wherein $R^1$ is a saturated or unsaturated, aliphatic hydrocarbon radical having from about 7 to 21, preferably from about 11 to 17 carbon atoms; $R^2$ represents a methylene or ethylene group; and m is 1, 2, or 3.

Specific examples of said amides are mono-ethanol amine coconut fatty acid amide and diethanol amine dodecyl fatty acid amide. These acyl moieties may be derived from naturally occurring glycerides, e.g., coconut oil, palm oil, soybean oil, and tallow, but can be derived synthetically, e.g., by the oxidation of petroleum or by hydrogenation of carbon monoxide by the Fischer-Tropsch process. The monoethanol amides and diethanolamides of $C_{12-14}$ fatty acids are preferred. Additionally, amine oxide semi-polar nonionic surfactants as discussed above can also serve as suds boosters.

Optional Ingredients

The detergent compositions described herein may also contain conventional optional ingredients which are usually used in additive levels of below about 25% include opacifiers, antioxidants, dyes, perfumes, optical brighteners, and the like. The following are intended only to be illustrations of such ingredients, more examamples of which will readily come to the mind of the skilled formulator.

Optional enzymes such as protease, lipase and/or amylase may be added to the compositions of the present invention as described in U.S. Pat. No. 5,559,400, which is incorporated herein by reference. Such enzymes provide additional cleaning benefits as well as promote the health of the skin and to provide the consumer with a perceived mildness or skin feel/appearance advantage over other similar detergent compositions which do not contain proteases.

Detergency builders may also be present in amounts from 0% to about 50%, preferably from about 2% to about 30%, most preferably from about 5% to about 15%. It is typical in light duty liquid or gel dishwashing, detergent compositions to have no detergent builder present. However, certain compositions containing magnesium or calcium ions may require the additional presence of low levels of, preferably from 0 to about 10%, more preferably from about 0.5% to about 3%, chelating agents selected from the group consisting of bicine/bis(2-ethanol)blycine), citrate N-(2-hydroxylethyl) iminodiacetic acid (HIDA), N-(2,3-dihydroxypropyl) iminodiacetic acid (GIDA), and their alkali metal salts. Some of these chelating agents are also identified in the art as detergency builders. The compositions of this invention may contain for chelating and detergency purposes from about 0.001% to about 15% of certain alkylpolyethoxypolycarboxlyate surfactants of the general formula:

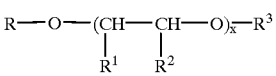

wherein R is a $C_{6\ to\ 18}$ alkyl group, x ranges from about 1 to about 24, $R^1$ or $R^2$ are selected from the group consisting of hydrogen, methyl acid radical succinic acid radical hydroxy succinic acid radical, and mixtures thereof, wherein at least one $R^1$ or $R^2$ is a succinic acid and/or hydroxysuccinic acid radical. An example of a commercially available alkylpolyethoxypolycarboxylate which can be employed in the present invention is POLN-TERGENT C, Olin Corporation, Cheshire, Conn.

The alkylpolyethoxypolycarboxylate surfactant is selected on the basis of its degree of hydrophilicity. A balance of carboxylation and ethoxylation is required in the alkylpolyethoxypolycarboxylate in order to achieve maximum chelating benefits without affecting the cleaning benefits which is associated with the divalent ions or the sudsing of the liquid or gel dishwashing detergent compositions. The number of carboxylate groups dictates the chelating ability, too much carboxylation will result in too strong a chelator and prevent cleaning by the divalent ions. A high degree of ethoxylation is desired for mildness and solubility; however, too high a level will affect sudsing. Therefore, an alkylpolyethoxypolycarboxylate with a modest degree of ethoxylation and minimal carboxylation is desirable.

Other desirable, optional ingredients include inorganic salts, such as sodium chloride, potassium chloride, enzymes etc.

Method Aspect

In the method aspect of this invention, substrates, most typically soiled dishes, are contacted with an effective amount of the detergent composition of the present invention. In the cases of soiled dishes, the effective amount of the detergent composition will be about 0.5 ml. to about 20 ml. (per 25 dishes being treated), preferably from about 3 ml. to about 10 ml. The actual amount of liquid detergent composition used will be based on the judgment of user, and will typically depend upon factors such as the particular product formulation of the composition, including the concentration of active ingredient in the composition, the number of soiled dishes to be cleaned, the degree of soiling on the dishes, and the like. The particular product formulation, in turn, will depend upon a number of factors, such as the intended market (i.e., U.S., Europe, Japan, etc.) for the composition product. The following are examples of typical methods in which the detergent compositions of the present invention may be used to clean dishes. These examples are for illustrative purposes and are not intended to be limiting.

In a typical U.S. application, from about 3 ml. to about 15 ml., preferably from about 5 ml. to about 10 ml. of a liquid detergent composition is combined with from about 1,000 ml. to about 10,000 ml., more typically from about 3,000 ml. to about 5,000 ml. of water in a sink having a volumetric capacity in the range of from about 5,000 ml. to about 20,000 ml., more typically from about 10,000 ml. to about 15,000 ml. The detergent composition has a surfactant mixture concentration of from about 21% to about 44% by weight, preferably from about 25% to about 40% by weight. The soiled dishes are immersed in the sink containing the detergent composition and water, where they are cleaned by contacting the soiled surface of the dish with a cloth, sponge, or similar article. The cloth, sponge, or similar article may be immersed in the detergent composition and water mixture prior to being contacted with the dish surface, and is typically contacted with the dish surface for a period of time ranging from about 1 to about 10 seconds, although the actual time will vary with each application and user. The contacting of the cloth, sponge, or similar article to the dish surface is preferably accompanied by a concurrent scrubbing of the dish surface.

In a typical European market application, from about 3 ml. to about 15 ml., preferably from about 3 ml. to about 10 ml. of a liquid detergent composition is combined with from about 1,000 ml. to about 10.000 ml., more typically from about 3,000 ml. to about 5,000 ml. of water in a sink having a volumetric capacity in the range of from about 5,000 ml. to about 20,000 ml., more typically from about 10,000 ml. to about 15,000 ml. The detergent composition has a surfactant mixture concentration of from about 20% to about 50% by weight, preferably from about 30% to about 40%, by weight. The soiled dishes are immersed in the sink containing the detergent composition and water, where they are cleaned by contacting the soiled surface of the dish with a cloth, sponge, or similar article. The cloth, sponge, or similar article may be immersed in the detergent composition and water mixture prior to being contacted with the dish surface, and is typically contacted with the dish surface for a period of time ranging from about 1 to about 10 seconds, although the actual time will vary with each application and user. The contacting of the cloth, sponge, or similar article to the dish surface is preferably accompanied by a concurrent scrubbing of the dish surface.

In a typical Latin American and Japanese market application, from about 1 ml. to about 50 ml., preferably from about 2 ml. to about 10 ml. of a detergent composition is combined with from about 50 ml. to about 2,000 ml., more typically from about 100 ml. to about 1,000 ml. of water in a bowl having a volumetric capacity in the range of from about 500 ml. to about 5,000 ml., more typically from about 500 ml. to about 2,000 ml. The detergent composition has a surfactant mixture concentration of from about 5% to about 40% by weight, preferably from about 10% to about 30% by weight. The soiled dishes are cleaned by contacting the soiled surface of the dish with a cloth, sponge, or similar article. The cloth, sponge, or similar article may be immersed in the detergent composition and water mixture prior to being contacted with the dish surface, and is typically contacted with the dish surface for a period of time ranging from about 1 to about 10 seconds, although the actual time will vary with each application and user. The contacting of the cloth, sponge, or similar article to the dish surface is preferably accompanied by a concurrent scrubbing of the dish surface.

Another method of use will comprise immersing the soiled dishes into a water bath without any liquid dishwashing detergent. A device for absorbing liquid dishwashing detergent, such as a sponge, is placed directly into a separate quantity of undiluted liquid dishwashing composition for a period of time typically ranging from about 1 to about 5 seconds. The absorbing device, and consequently the undiluted liquid dishwashing composition, is then contacted individually to the surface of each of the soiled dishes to remove said soiling. The absorbing device is typically contacted with each dish surface for a period of time range from about 1 to about 10 seconds, although the actual time of application will be dependent upon factors such as the degree of soiling of the dish. The contacting of the absorbing device to the dish surface is preferably accompanied by concurrent scrubbing.

The following examples are illustrative of the present invention, but are not meant to limit or otherwise define its scope. All parts, percentages and ratios used herein are expressed as percent weight of the composition unless otherwise specified.

EXAMPLE 1

A light-duty liquid dishwashing detergent formula having the following composition is prepared:

| | % By Weight | | |
|---|---|---|---|
| Ingredient | A | B | C |
| Sodium $C_{12-13}$ alkyl ethoxy (1.4) sulfate | 34.2000 | 34.2000 | 34.2000 |
| *Amine oxide | 5.2000 | 5.2000 | 5.2000 |
| *Iodine | 0.0046 | 0.0046 | 0.0000 |
| *potassium iodide | 0.0000 | 0.0050 | 2.0000 |
| linear glucose amide | 1.4300 | 1.4300 | 1.4300 |
| Calcium/sodium xylene sulfonate | 4.7500 | 4.7500 | 4.7500 |
| Magnesium chloride | 2.6800 | 2.6800 | 2.6800 |
| Neodol (C11E-9) | 0.9500 | 0.9500 | 0.9500 |
| Tetronic 704 | 0.3800 | 0.3800 | 0.3800 |
| Ethanol | 5.3000 | 5.3000 | 5.3000 |
| Water | Balance | Balance | Balance |

*Amine oxide, potassium iodide and iodine were premixed to form an iodophor.

A Modified Germicidal Spray Test was conducted in which substrates were coated with dilute solutions of *Staphylococcus aureus* and *Escherichia coli* and then treated with LDL formulas containing iodophors, and LDL formulas without iodophors. The formulas with iodophors showed significantly better disinfection performance over the formulas without iodophors, particular in regards to the *Staphylococcus aureus* bacteria.

Accordingly, having thus described the invention in detail, it will be obvious to those skilled in the art that various changes may be made without departing from the scope of the invention and the invention is not to be considered limited to what is described in the specification.

What is claimed is:

1. A light duty liquid detergent composition characterized by weight of the composition:
   (1) from 0.001% to 2.0% of iodine ions, characterized in that at least a portion of the iodine ions are complexed iodine that is complexed with a complexing surfactant selected from the group consisting of amido propyl betaines, derivatives of aliphatic or heterocylclic secondary and tertiary amines, semi-polar nonionic surfactants, alcohol ethoxylates and mixtures thereof;
   (2) from 5% to 90% of an uncomplexed surfactant selected form the group consisting of anionic surfactants, nonionic surfactants, semi-polar nonionic surfactants and mixtures thereof; and (3) from 5% to 50% water;
characterized in that the light duty liquid detergent composition has a pH of between 7 and 10.

2. A composition according to claim 1 characterized in that at least a portion of the iodine ions are added to the composition in the form of an iodine powder.

3. A composition according to claim 1 characterized in that at least a portion of the iodine ions are added to the composition as an iodide in the form of a compound selected from the group consisting of KI, NaI, KOI, NaOI, Ca(OI)$_2$.

4. A composition according to claim 1 characterized in that the complexing surfactant is a semi-polar amine oxide.

5. A composition according to claim 1 characterized in that a portion of the complexed iodine is complexed with a nonionic surfactant.

6. A composition according to claim 1 characterized in that the nonionic surfactant is an alcohol ethoxylate of the formula:

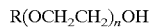

characterized in that R is a $C_{12-16}$ alkyl group and n ranges from 0 to 10.

7. A composition according to claim 1 characterized in that the complexed iodine and the complexing surfactant are in a weight ratio of from 1:20 to 1:10.

8. A method for disinfecting a microbe containing substrate in a manual dishwashing operation characterized by the steps of:

(a) contacting the substrate with a light duty liquid detergent composition prepared according to claim 1; and (b) allowing the detergent composition to remain in contact with the substrate for a sufficient time to significantly reduce the amount of microbes on the substrate.

9. A method according to claim 8, characterized in that the detergent composition is applied to the substrate by direct application.

10. A method according to claim 9, characterized in that the detergent composition is applied to the substrate with no more than 90% dilution with water.

* * * * *